United States Patent
Cox et al.

(10) Patent No.: US 9,952,167 B1
(45) Date of Patent: Apr. 24, 2018

(54) METHOD AND DEVICE TO AID IN THE INSPECTION AND CERTIFICATION OF HARVESTED FOOD FOR HUMAN CONSUMPTION

(71) Applicant: Seafood Analytics, Clinton Township, MI (US)

(72) Inventors: Marlin Keith Cox, Juneau, AK (US); Rudolph J. Liedtke, Grosse Pointe Park, MI (US)

(73) Assignee: Seafood Analytics, Clinton Township, MI (US)

( * ) Notice: Subject to any disclaimer, the term of this patent is extended or adjusted under 35 U.S.C. 154(b) by 0 days.

(21) Appl. No.: 14/511,807

(22) Filed: Oct. 10, 2014

Related U.S. Application Data

(60) Provisional application No. 62/052,182, filed on Sep. 18, 2014, provisional application No. 61/949,555, filed on Mar. 7, 2014.

(51) Int. Cl.
  *G01N 27/02* (2006.01)
  *A61B 5/053* (2006.01)
  (Continued)

(52) U.S. Cl.
  CPC ........... *G01N 27/02* (2013.01); *A61B 5/0531* (2013.01); *G01N 33/12* (2013.01); *G01R 1/06733* (2013.01)

(58) Field of Classification Search
  CPC ...... A61B 2562/0209; A61B 2562/043; A61B 5/0492; A61N 1/0551; A61N 1/36014; G01N 33/5085
  See application file for complete search history.

(56) References Cited

U.S. PATENT DOCUMENTS

| | | | |
|---|---|---|---|
| 3,320,946 A | 5/1967 | Dethloff et al. | 128/2.1 |
| 3,665,302 A | 5/1972 | Lees et al. | 324/64 |

(Continued)

FOREIGN PATENT DOCUMENTS

EP   0187392   12/1985   ............. G01N 33/12

OTHER PUBLICATIONS

Caldarone, Elaine M. et al., "Evaluation of Bioelectrical Impedance Analysis and Fulton's Condition Factor as Nonlethal Techniques for Estimating Short-Term Responses in Postsmolt Atlantic Salmon (*Salmo salar*) to Food Availability", Fishery Bulletin, Jan. 2012, pp. 257-270.

(Continued)

*Primary Examiner* — Michele L Jacobson
*Assistant Examiner* — Preston Smith
(74) *Attorney, Agent, or Firm* — Christopher P. Maiorana, PC

(57) ABSTRACT

An apparatus includes an array of compression electrodes and an analysis circuit. The array of compression electrodes includes a pair of outer compression electrodes and a pair of inner compression electrodes. Each of the electrodes includes a contact pad and may be configured to automatically adjust to follow a contour of an object while maintaining contact of the contact pad with a surface of the object. The analysis circuit can be coupled to the array of compression electrodes. The analysis circuit may be configured to automatically make a bioelectrical impedance measurement using the array of compression electrodes and generate a value representing a cell integrity of said object.

20 Claims, 12 Drawing Sheets

(51) Int. Cl.
*G01N 33/12* (2006.01)
*G01R 1/067* (2006.01)

(56) References Cited

U.S. PATENT DOCUMENTS

| | | | |
|---|---|---|---|
| 4,758,778 A | 7/1988 | Kristinsson | 324/65 R |
| 4,865,039 A * | 9/1989 | Dunseath, Jr. | A61B 5/0408 |
| | | | 128/902 |
| 6,631,292 B1 | 10/2003 | Liedtke | 600/547 |
| 6,946,838 B2 * | 9/2005 | Corver | G01N 24/085 |
| | | | 324/306 |
| 7,003,346 B2 | 2/2006 | Singer | 600/547 |
| 7,136,697 B2 | 11/2006 | Singer | 600/547 |
| 8,150,633 B2 | 4/2012 | Burke et al. | 702/19 |
| 8,457,904 B2 | 6/2013 | Burke et al. | 702/19 |
| 2005/0203433 A1 | 9/2005 | Singer | 600/547 |
| 2006/0292550 A1 * | 12/2006 | Cox | G01N 33/5085 |
| | | | 435/4 |
| 2007/0104840 A1 | 5/2007 | Singer et al. | 426/231 |
| 2007/0163676 A1 * | 7/2007 | Butler | C23C 8/22 |
| | | | 148/209 |
| 2008/0224716 A1 | 9/2008 | Singer et al. | 324/629 |
| 2008/0306402 A1 | 12/2008 | Singer | 600/547 |
| 2010/0081961 A1 | 4/2010 | Cox | 600/547 |
| 2010/0086655 A1 | 4/2010 | Singer | 426/232 |
| 2010/0182021 A1 | 7/2010 | Singer | 324/692 |
| 2010/0245555 A1 | 9/2010 | Talluri et al. | 348/77 |
| 2011/0276108 A1 * | 11/2011 | Crowe | A61N 1/0452 |
| | | | 607/48 |
| 2012/0101358 A1 * | 4/2012 | Boettcher | A61B 5/04001 |
| | | | 600/384 |
| 2012/0107461 A1 | 6/2012 | Burke et al. | 426/231 |
| 2012/0302841 A1 | 11/2012 | Coressel et al. | 600/301 |

OTHER PUBLICATIONS

Cox, Keith M., "Bioelectrical Impedance Analysis Measures of Body Composition and Condition, and its Sensitivity to the Freezing Process", Journal of Aquatic Food Product Technology, Dec. 18, 2013, pp. 1-24.

Gupta et al., "Bioelectrical Impedance Phase Angle in Clinical Practice: Implications for Prognosis in Advanced Colorectal Cancer," American Journal of Clinical Nutrition, vol. 80 (2004), pp. 1634-1638.

Ravishankar et al., "Use of Torrymeter for Measurement of Freshness of Some Commercially Important Indian Marine Fishes," Indian Journal of Fisheries, vol. 41, No. 1, (Mar. 1994), pp. 28-32.

Pivarnik et al. "Freshness Assessment of Six New England Fish Species Using the Torrymeter," Journal of Food Science, vol. 55, No. 1, (1990), pp. 79-82.

Technical Manual; Distell Fish Freshness Meter; Model Torrymeter, Distell.com, (2011), pp. 1-14.

* cited by examiner

METHOD AND DEVICE TO AID IN THE INSPECTION AND CERTIFICATION OF HARVESTED FOOD FOR HUMAN CONSUMPTION

This application relates to U.S. Ser. No. 61/949,555, filed Mar. 7, 2014 and relates to U.S. Ser. No. 62/052,182, filed Sep. 18, 2014, which are incorporated by reference in their entirety.

FIELD OF THE INVENTION

The present invention relates to food inspection generally and, more particularly, to a method and/or apparatus to aid in the inspection and certification of harvested food for human consumption.

BACKGROUND OF THE INVENTION

Determining condition and quality of foodstuffs is important to the consumer and to marketability of the foodstuff. Making an assessment of foodstuff quality is essential to guarantee a safe and wholesome product for human consumption. In the case of seafood, current quality management systems, i.e., the National Oceanic and Atmospheric Association (NOAA) Seafood Inspection program and the federal Hazard Analysis and Critical Control Point (HACCP), rely heavily on good record keeping.

A direct measurement of the condition of fish by biological or chemical analysis is not practiced because of complexity, cost, and time. Therefore, more subjective methods, such as Quality Index Method (QIM), are used throughout the catch to consumption chain. These subjective practices are primarily based on olfactory, tactile, and visual scores of fish. The time period after harvest is important, because fish tissue begins to decompose after catching, harvesting, and killing, and shelf life thereafter is dependent on species and post harvest practices. A shorter shelf life can result from temperature, handling, and product abuse.

The professional care of the product from harvesting to consumption can be monitored by studying the electrical properties of the product. Measuring electrical properties of fish tissue is a quantitative method of evaluating the fish after harvest. Electrical measures can quantitatively show that colder temperatures slow the natural degradation process of tissues that involve the production of protease enzymes that denature the proteins located in the cell membrane. Freezing on the other hand, involves the induction of large osmotic differences that rupture the cell membranes after thawing. This causes an influx of electrolytes from the cytoplasm into interstitial spaces and reducing shelf life significantly.

It would be desirable to have a method and device to aid in the inspection and certification of harvested food for human consumption.

SUMMARY OF THE INVENTION

The present invention concerns an apparatus including an array of compression electrodes and an analysis circuit. The array of compression electrodes includes a pair of outer compression electrodes and a pair of inner compression electrodes. Each of the compression electrodes includes a contact pad and automatically adjusts to follow a contour of an object while maintaining contact of the contact pad with a surface of the object. The analysis circuit may be coupled to the array of compression electrodes. The analysis circuit may be configured to automatically make a bioelectrical impedance measurement using the array of compression electrodes and generate a value representative of a cell integrity of the object.

The objects, features and advantages of the present invention include providing a method and device to aid in the inspection and certification of harvested food for human consumption that may (i) provide a reliable and repeatable measurement of cell integrity of a food specimen, (ii) be non-invasive, non-damaging, and non-contaminating to a food specimen, (iii) provide repeatable measurements that are independent of the person making the measurement, (iv) facilitate implementation of a harvest-to-table value chain (traceability), (v) provide a reliable measurement to inform consumers of food quality, (vi) be integrated into a control system of a food handling system, (vii) provide a quickly generated indicator of the cellular integrity a food specimen, and/or (viii) be implemented in a portable handheld apparatus.

BRIEF DESCRIPTION OF THE DRAWINGS

These and other objects, features and advantages of the present invention will be apparent from the following detailed description and the appended claims and drawings in which:

DETAILED DESCRIPTION OF THE PREFERRED EMBODIMENTS

Figure 1:
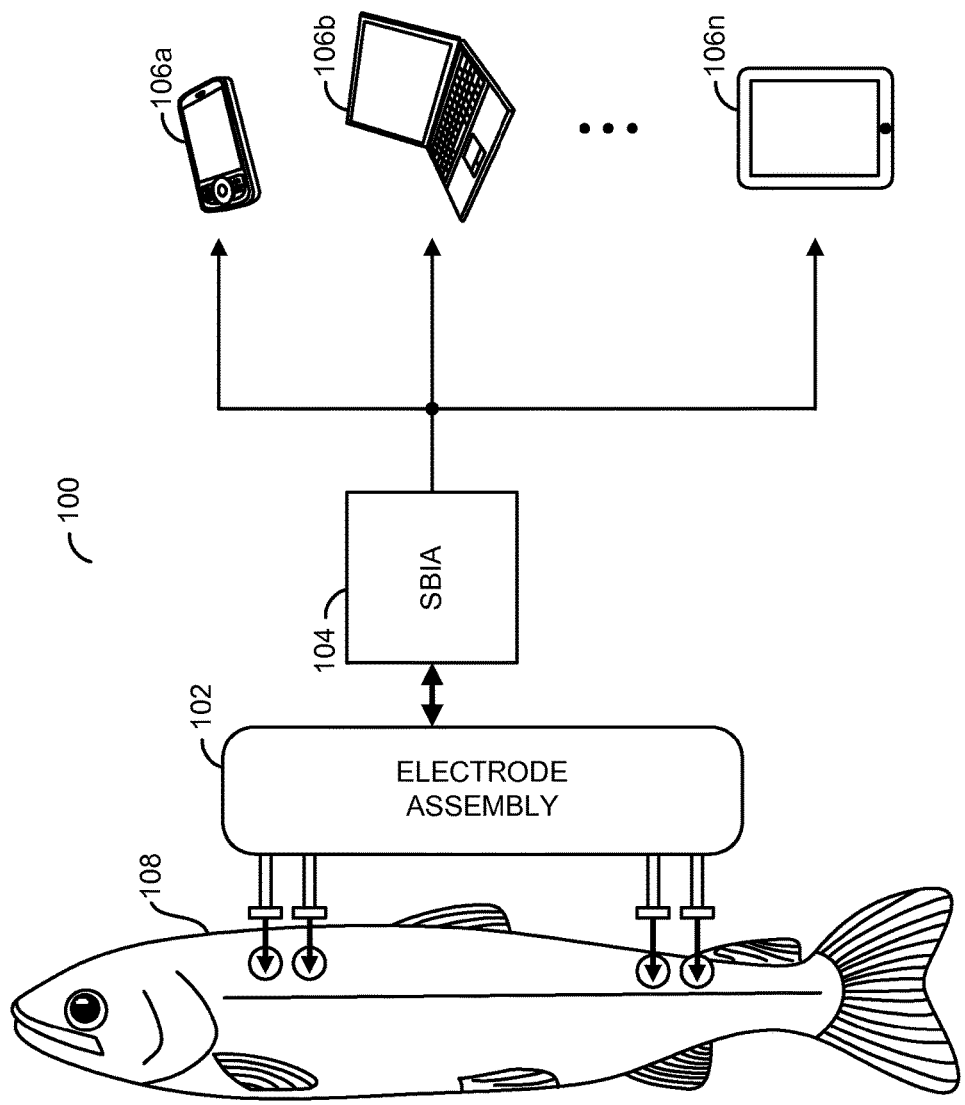
FIG. 1 is a diagram illustrating a system in accordance with an embodiment of the invention.

Referring to FIG. 1, a diagram of a system 100 is shown in accordance with an example embodiment of the present invention. In various embodiments, the system 100 may comprise an electrode assembly 102, an analysis circuit 104, and one or more electronic devices 106a-106n. The electrode assembly 102 is configured to connect the analysis circuit 104 to a subject (specimen) 108. The specimen may be any portion of food for human consumption. The food specimen may be whole (e.g., fish, banana, lemon, peach, cucumber, etc.) or a portioned (e.g., fish filet, beef filet or steak, pork chop, etc.). The connection is made via the skin (or flesh) of the specimen 108 and is non-invasive, non-damaging, and non-contaminating.

In various embodiments, the electrode assembly 102 comprises an array of compression electrodes. A base of each compression electrode comprises a conductive disk. In various embodiments, the electrodes are made of stainless steel or other corrosion-resistant, conductive (e.g., metallic, etc.) material. In various embodiments, spacing between the compression electrodes in the electrode array is fixed generally (e.g., based upon the specimen being measured). A number of models of the electrode assembly 102 may be manufactured to provide a variety of fixed electrode spacings. In some embodiments, electrodes positions may be adjusted according to the particular specimen being measured (assessed). The electrode assembly 102 generally provides measurement accuracy and repeatability of cell integrity results. In an example taking measurements of a fish, the electrode array may be placed along an imaginary line running above a lateral line, below dorsal and adipose fin bases, starting behind a posterior edge of the operculum, and running to a leading edge of the adipose fin. However, other locations may also be used (e.g., along the lateral line, on the belly, etc.).

In various embodiments, the analysis circuit 104 comprises an analog portion (e.g., BIA circuitry) and a digital portion (e.g., hardware and/or software) configured to automatically generate and store resistance and reactance data. The analysis circuit 104 is further configured to communicate the resistance and reactance data to the one or more electronic devices 106a-106n. The resistance and reactance data may be communicated concurrently with the testing (e.g., on a factory floor, etc.) or downloaded at a later time (e.g., at a tender when the catch is transferred from a fishing boat, at a processing plant after transfer from the tender, etc.). In addition to the BIA data, the analysis circuit 104 may be further configured to collect and store information (e.g., length, weight, species, gender, etc.) about the particular subject 108. In one example, the resistance and reactance values are communicated in a comma separated value (CSV) format.

In some embodiments, the analysis circuit 104 may be connected to the electronic devices 106a-106n via a serial connection such as a universal serial bus (USB), IEEE 802.2 Ethernet, or other wired connection. In some embodiments, the analysis circuit 104 may be connected to the electronic devices 106a-106n via a wireless protocol (e.g., IEEE 802.11a/b/g/n, IEEE 802.15.1 ZigBee, IEEE 802.15.4 BlueTooth®, etc.). However, other communications protocols may be implemented accordingly to meet the design criteria of a particular implementation. In one example, the analysis circuit 104 may be implemented using an analyzer as described in U.S. Pat. No. 6,631,292, which is incorporated by reference in its entirety. In some embodiments, the functionality of the analysis circuit 104 and one of the electronic devices 106a-106n may be implemented in a single handheld unit (e.g., described below in connection with FIG. 8).

The electronic devices 106a-106n may comprise one or more of a mobile computing device 106a, a laptop computer 106b, a desktop computer, a tablet computer 106n, etc. In various embodiments, the electronic devices 106a-106n are configured by application software to calculate a Certified Quality Number using the information about the specimen and the bioelectrical resistance and reactance measurements received from the analysis circuit 104, and a number of predetermined coefficients (e.g., stored in a lookup table). The electronic devices 106a-106n may be configured by the application software to generate a report presenting the certified quality number(s) (e.g., on a display screen, as a PDF formatted report, as a printed report, etc.) in numerical and/or graphical form.

When an alternating current (AC) is introduced into living tissue it follows two pathways. The real impedance vector (resistance) will follow the conductive ions of electrolytes (Na+, K+, CA+, Mg+) within interstitial spaces. The imaginary (capacitive reactance) impedance vector will follow the path of nonconductive phospholipid bilayers that make up cell membranes. A simple analogy would be a capacitor and resistor wired in parallel. Therefore, the electrical properties of tissue are measured series equivalent impedance vectors resulting from the introduction of a constant magnitude alternating current into the tissue. The two vectors are imaginary and real complex magnitudes where their ratio (I/R) is proportional to cellular integrity. The lower the number the shorter the remaining time before decomposition. Zero meaning there is no time left and the fish should not be consumed.

When tissue ages, resistance (real vector) decreases with the influx of conductive ions from compromised cells into the interstitial spaces. In natural post-mortem degradation, lactic acid accumulates in the muscle and protease (protein enzymes) activity increases that eventually compromise cell membrane integrity. Capacitive reactance (e.g., the imaginary vector) decreases with cell membrane losses and volume.

All biological living tissues have specific electrical characteristics. Example resistance and capacitive reactance measurements for a number of food specimens are summarized in the following TABLE 1:

TABLE 1

| Specimen | R | Xc |
| --- | --- | --- |
| Sweet Potato | 1100 | 1300 |
| Cucumber | 800 | 750 |
| Red Bell Pepper | 460 | 1300 |
| Yellow Bell Pepper | 1721 | 1325 |
| Banana | 404 | 685 |
| Apple (inside) | 605 | 448 |
| Peach | 1372 | 1281 |
| Lemon | 922 | 1238 |
| Onion (inside) | 430 | 536 |
| Potato (white) | 630 | 1330 |
| Corn | 700 | 486 |
| Yellow Squash | 524 | 282 |
| Beets | 1017 | 998 |
| Cheese | 66.4 | −4.4 |
| Ham | 184 | −6.2 |
| Salmon | 41 | 24.6 |
| Beef (Brisket) | 23.3 | 1.1 |
| Lingcod | 89.2 | 6.3 |
| Pacific Cod | 51 | 15.6 |

Humans have a specific reactance to resistance ratio that is age and disease dependent. The ratio decreases with age and approaches zero when the patient is near death.

The ratio of capacitive reactance (Xc) to resistance (R) is referred to herein as an "Omega Ratio" in celebration of the Ohm symbol and the German physicist Georg Ohm (1789-1854). The Omega Ratio values can vary for different foodstuffs. Harvested fish have different Omega Ratio values depending on their species. For example, a Salmon may have an Omega Ratio of 0.675, while a Cod may have an Omega Ratio of 0.404. Thus, the Omega Ratios of Salmon and Cod may differ by 0.271. However, a simple lookup table may be used to normalize ratios between species with a coefficient and offset (Y=AX+B) so that "end time" is highly predictable for any fish species. The Omega Ratio may be used to determine various qualitative ratings (e.g., grade, rate of decomposition, shelf life remaining, rejection points, etc.).

In various embodiments, the Omega Ratio may be used to generate a value representative of cellular integrity of a food specimen. In some embodiments, the value is implemented as a Certified Quality Number (CQN). The CQN value may be determined, in one example, according to the following Equation 1:

$$CQN = \frac{Xc}{R} \times \frac{180}{\Pi} \times \frac{KS}{SSCI}, \qquad \text{Eq. 1}$$

where SSCI represents a species specific cell integrity value (or coefficient) and KS represents a desired range of the CQN value. The SSCI value for each species or food type may be determined by testing a number of samples of each species or food type to determine a value corresponding to maximum cell integrity. A lookup table may be generated containing SSCI values for a plurality of foodstuff types and sizes. In one example, the value KS may be set equal to ten (e.g., KS=10) to provide a CQN with a range of 0-10. In another example, KS=100 yields a CQN with a range of 0-100. In some embodiments, the Omega Ratio (Xc/R) may be generated through a number of iterations (e.g., repeated measurements).

In general, the sensitivity for any measurement is dependent on its repeatability. If repeatability can not be demonstrated then accurate value changes are useless. Some measuring techniques (e.g., Phase Angle) lose sensitivity at their measurement extremes. Unfortunately, sensitivity is most important at the extremes. The Certified Quality Number is scalable and maintains sensitivity over the entire range of measurement, even at the extremes. In one example, a test was performed using an RJL Systems/Science Quantum IV, mechanically modified for compression electrodes, to make repeated measurements on the same fish in different locations on the fish using an array of surface compression electrodes in accordance with an embodiment of the invention. The measurements showed good repeatability. The same repeatability has also been documented on multiple fish species.

In various embodiments, a measuring instrument in accordance with an embodiment of the invention may also include a real-time clock and calendar with a local memory to store and time stamp each fish measurement. Communications may include an isolated USB port and Bluetooth® allowing connection, to a PC, I-PAD, smart phone, etc., to download the saved data. Battery life is based on Lithium-Ion technology and has a 24 hour continuous use cycle. In some embodiments, GPS (Global Positioning System) or GNSS (Global Navigation Satellite System) information is collected for determining the location of the harvested fish.

The time remaining after a fish has been harvested and not frozen can be quantified by measuring the ratio of the impedance vectors (capacitive reactance and resistance). When this Omega Ratio is zero the fish has lysed all its cells due to decomposition and can not be consumed. The impedance measurement interface is a non-invasive, non-damaging, non-contaminating contact through the fish scales using stainless steel compression electrodes. These electrodes inherently follow the contour of the fish and create a highly repeatable electrical measurement that accurately reflects the condition of the fish and is independent of the person making the measurement.

The instrumentation in accordance with embodiments of the invention can be used at every level of foodstuff harvesting and processing. In the example of fish (and seafood generally), this includes the fishing and tender boats, processing plant, wholesaler, retailer, and finally the chef who is cooking the fish. All measurements are catalogued and time stamped in the instrument to conform to any quality assurance and/or traceability program that begins on the fishing boat. Automation of these electrical impedance parameters at the processing plant level can be of prime importance because each fish is tested for quality before they are filleted, frozen, and packaged.

Figure 2:
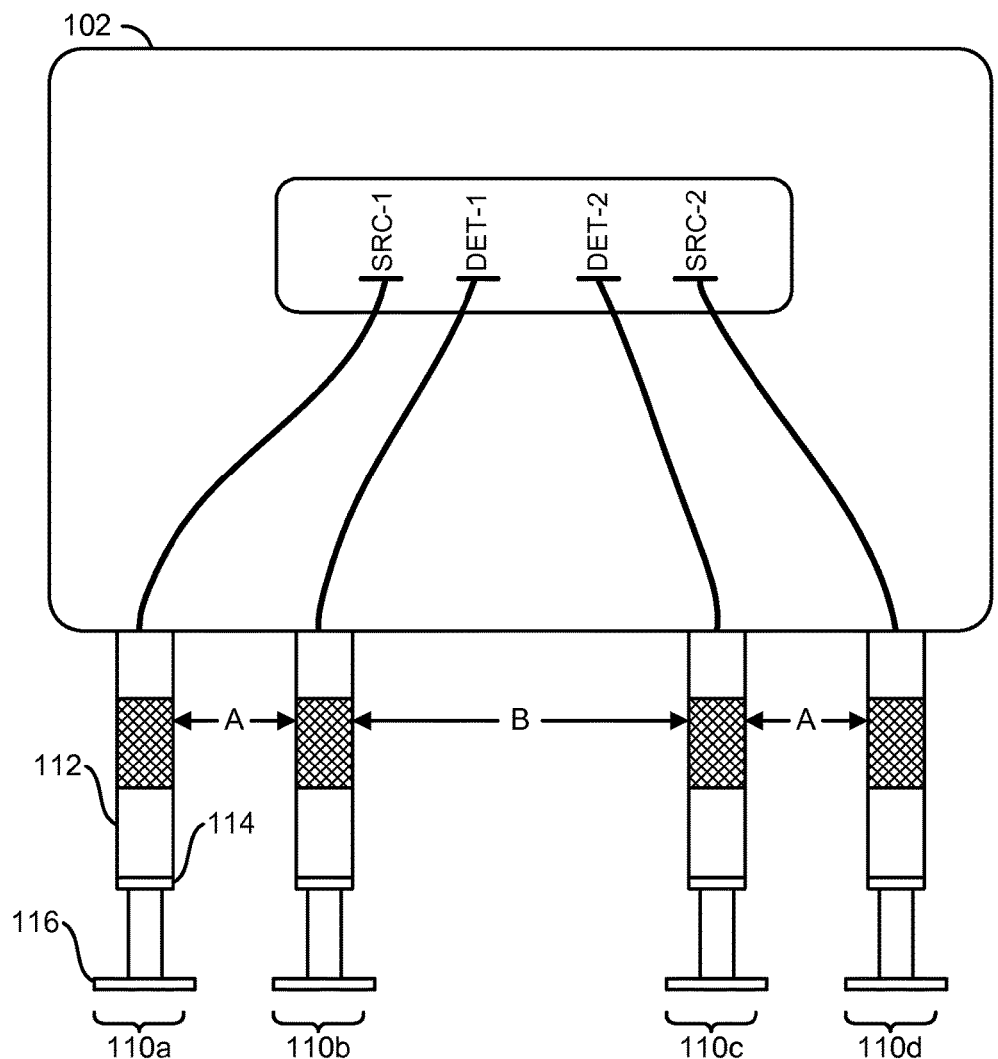
FIG. 2 is a diagram illustrating an example implementation of an electrode assembly of FIG. 1.

Referring to FIG. 2, a diagram is shown illustrating an example implementation of the electrode assembly 102 of FIG. 1. In a four electrode embodiment, outer electrodes 110a and 110d are configured as signal injection electrodes (e.g., connected to terminals SRC-1 and SRC-2, respectively) and inner electrodes 110b and 110c are configured as detecting electrodes (e.g., connected to terminals DET-1 and DET-2, respectively). The introduction and detection of the AC constant current is a four electrode circuit where the alternating current is a radio frequency. The constant current introduction is always outside (e.g., more distal) to the detecting electrodes and is referred to as tetrapolar impedance analysis.

In various embodiments, the electrode interface comprises four stainless steel spring-loaded compression electrodes that follow the contour of the specimen (e.g., a fish, etc.) being assessed. The non-invasive compression electrodes do not harm, contaminate, or pierce the skin of the fish. The non-invasive compression electrodes only touch the surface of the specimen and make a highly reliable measurement through the skin, rind, flesh, fish scales, etc. This is facilitated by an analysis circuit providing a broad range alternating current (AC) constant current source and extremely high detector input impedance. In various embodiments, the base of each compression electrode is a stainless steel disk that may range from approximately 1 mm to about 100 mm in diameter. The distances between the electrodes are generally fixed depending on the model. In various embodiments, a spacing between adjacent outer and inner electrodes has a first magnitude (e.g., A) and a spacing between the inner electrodes has a second magnitude (e.g., B). The spacing B is generally determine based on species.

The compression electrode array is generally scaled to approximate the size of the specimen. For example, larger specimens (e.g., Marlin fish, etc.) use larger electrodes and larger inter-electrode distances than smaller specimens (e.g., peach, sardine, etc.). In various embodiments, electrode contact pad diameters may range from 1 to 100 mm. The distance A between each signal and detecting electrode within an electrode pair may also vary with specimen size. In one example, the distance A may be implemented as approximately 10% of the total length of the specimen. The distance B between detecting electrodes also varies with the size of the specimen being measured. In one example, the distance B may be implemented as about 40% to 50% of the total length of the specimen. In some embodiments, the distance A between the source and detecting electrodes in an electrode pair may range from about 1 centimeter to about 1 meter, and the distance B between two detecting electrodes may range form 2 centimeters to 3 meters. However, other magnitudes may be used depending upon the size of the specimen.

In various embodiments, the stainless steel spring-loaded compression electrodes comprise a sleeve 112, a bearing 114, and a plunger 116. The plunger 116 includes the contact disk and a piston rod. In one example, the plunger 116 may be machined from a single piece of stainless steel (e.g., rod or bar stock) or assembled from stainless steel components.

Figure 3:
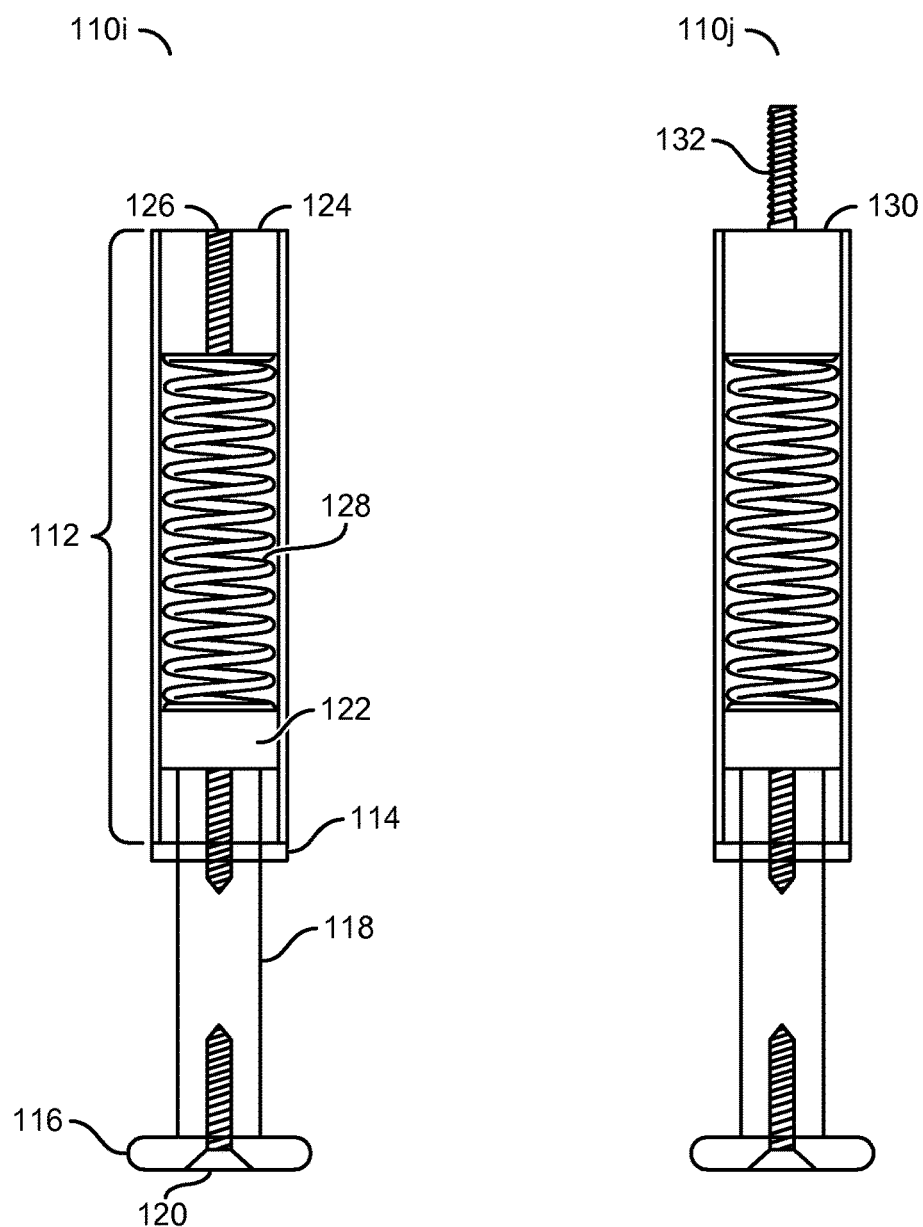
FIG. 3 is a diagram illustrating example implementations of compression electrodes of FIG. 2 in accordance with an embodiment of the invention.

Referring to FIG. 3, a diagram is shown illustrating example implementations of the compression electrodes of FIG. 2. In one example, an electrode 110*i* may be implemented with a female connecting end. In another example, an electrode 110*j* may be implemented with a male connecting end. In various embodiments, The compression electrodes may be fabricated using 303 stainless steel. The sleeve (or cylinder) 112 may be implemented with a ⅜"× 1⅞" stainless steel cylinder with an internal diameter (ID) reamed to about 0.3". The plunger 116 may be implemented as a separate ⅝" stainless steel pad attached to a piston rod 118 by a 6-32 stainless steel flat head screw 120. The piston rod 118 may be implemented as a ¼"×1⅛" stainless steel rod. One end of the piston rod 118 may have a 6-32 tap, the other end may have a 10-32 tap, and the 6-32 end may also have milled flats. The bearing 114 may be implemented as a ⅜" oil-impregnated sintered bronze bushing machined and press fit into the cylinder 112. A 10-32 nylon Allen head screw 122 may be machined to the reamed ID of the cylinder 112 and attached to the piston rod 118.

In the electrode 110*i*, a ⅜"×⅜" stainless steel end cap 124 with a 10-32 tap thru 126 may be machined and press fit into the end of the cylinder 112 opposite from the bearing 114 after a stainless steel spring 128 is inserted within the cylinder 112. In the electrode 110*j*, a ⅜"×⅜" stainless steel end cap 130 with a 10-32 stud 132 may be machined and press fit into the end of the cylinder 112 opposite from the bearing 114 after the stainless steel spring 128 is inserted within the cylinder 112. In one example, the spring 128 may provide a compressive force of about 200 grams.

Figure 4:
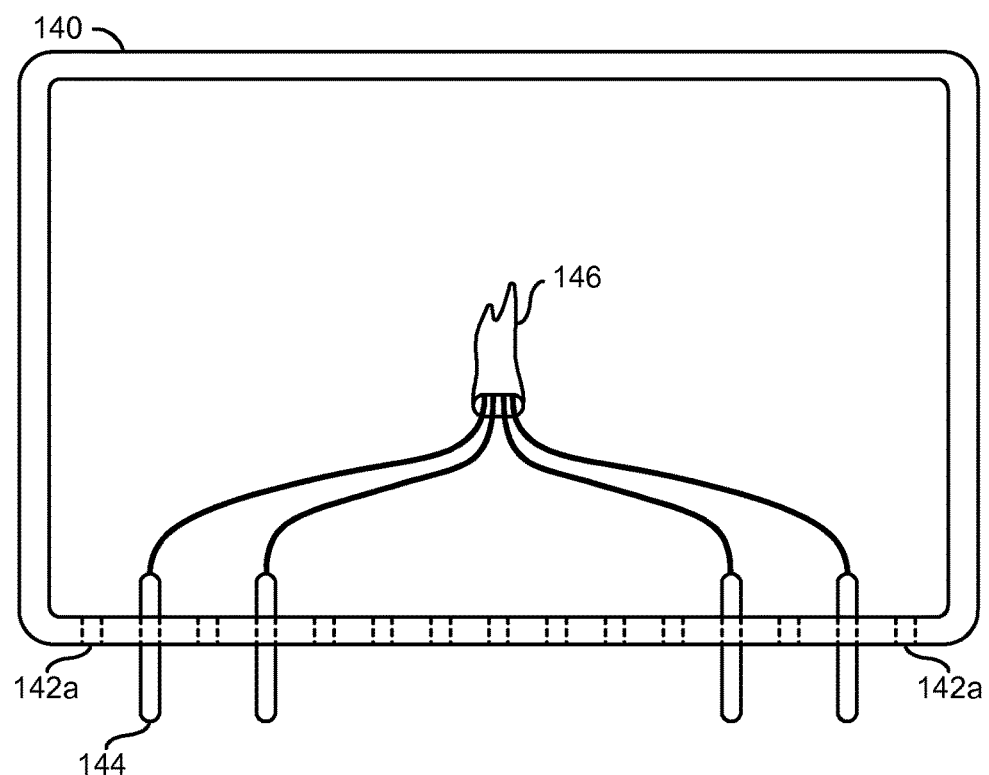
FIG. 4 is a diagram illustrating an example implementation of an electrode assembly providing multiple electrode positions.

Referring to FIG. 4, a diagram is shown illustrating an example implementation of an electrode assembly holder 140 in accordance with an example embodiment of the invention. The electrode assembly holder 140 provides multiple electrode positions allowing different electrode spacings to be selected for various specimens. In various embodiments, the electrode assembly holder 140 comprises a plurality of electrode slots 142*a*-142*n*. Electrodes 144 may be inserted into particular slots 142*a*-142*n* based on a desired electrode spacing. The electrodes 144 may be connected to the analysis circuit 104 via a cable 146. The electrode assembly holder 140 generally facilitates measuring Certified Quality Numbers when a variety of specimen sizes are to be measured with a single unit.

Figure 5:
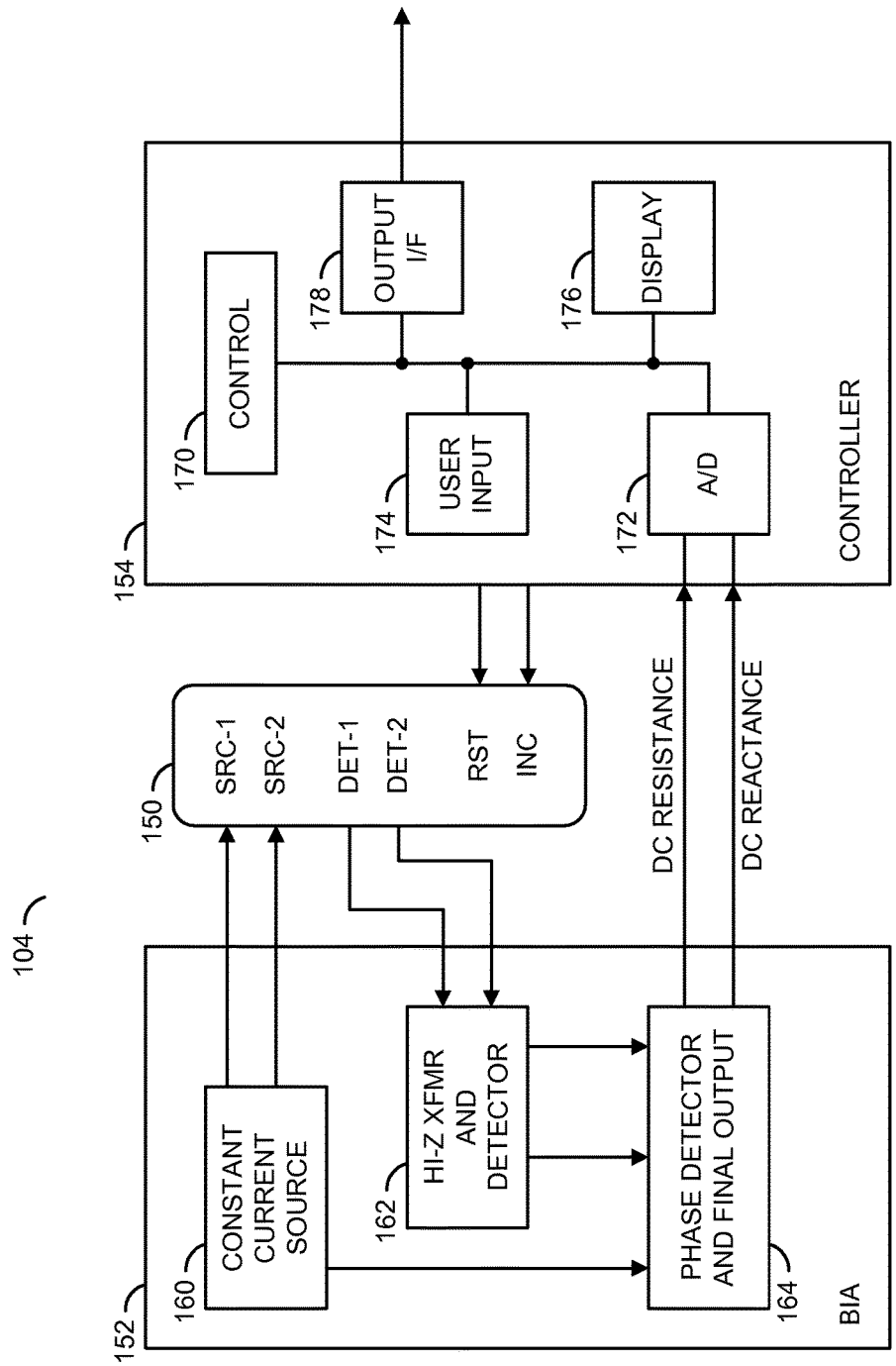
FIG. 5 is a diagram illustrating an example implementation of an analysis circuit of FIG. 1 in accordance with an embodiment of the invention.

Referring to FIG. 5, a diagram is shown illustrating an example implementation of the analysis circuit 104 of FIG. 1. The circuit 104 may be configured to connect to the circuit 104 using an interface 150. In one example, the circuit 104 may comprise a block (or circuit) 152 and a block (or circuit) 154. The block 152 may implement an analog portion of the circuit 104. The block 154 may implement a digital portion of the circuit 104. In one example, the circuit 152 implements circuitry for producing bioelectrical measurements comprising DC resistance and DC reactance values. In one example the circuit 154 implements an analog-to-digital (A/D) and controller portion of the circuit 104. The circuit 154 may be configured to convert analog resistance and reactance measurements made by the circuit 152 into digital resistance and reactance values that can be stored and/or communicated to the electronic devices 106*a*-106*n*.

In various embodiments, the circuit 152 comprises a block (or circuit) 160, a block (or circuit) 162, and a block (or circuit) 164. The block 160 may implement a constant current source and subject coupling transformer circuit. The block 162 may implement a high-impedance subject coupling transformer and detector circuit. The block 164 may implement a phase detector and final output circuit. The circuit 160 may provide the signals SRC-1 and SRC-2 to the interface 150. The circuit 162 may receive the signals DET-1 and DET-2 from the interface 150. The circuit 164 may be configured to generate analog resistance and reactance measurements in response to signals received from the circuits 160 and 162.

In various embodiments, the circuit 154 comprises a block (or circuit) 170, a block (or circuit) 172, a block (or circuit) 174, a block (or circuit) 176, and a block (or circuit) 178. The block 170 may implement a control circuit. The block 172 may implement an analog-to-digital (A/D) convertor circuit. The block 174 may implement a user input circuit. The block 176 may implement a display. The circuit 178 may implement an output interface (I/F). The control circuit 170 is generally configured to manage (i) operation of the analysis circuit 104 and (ii) communications with the user and the electronic devices 106*a*-106*n*. The circuit 172 may be configured to convert analog resistance and reactance measurements received from the circuit 152 to digital resistance and reactance values. The user input circuit 174 generally allows a user (technician) to enter information (e.g., age, species, length, weight, gender, etc.) about a subject and select menu items. The display circuit 176 generally allows the user to interact with the analysis circuit 104 via menu screens and read the measured resistance, reactance and certification values. The output I/F circuit 178 generally allows the subject information and measured resistance and reactance values to be communicated to external devices (e.g., by selecting a Send Data to External Device menu).

Figure 6:
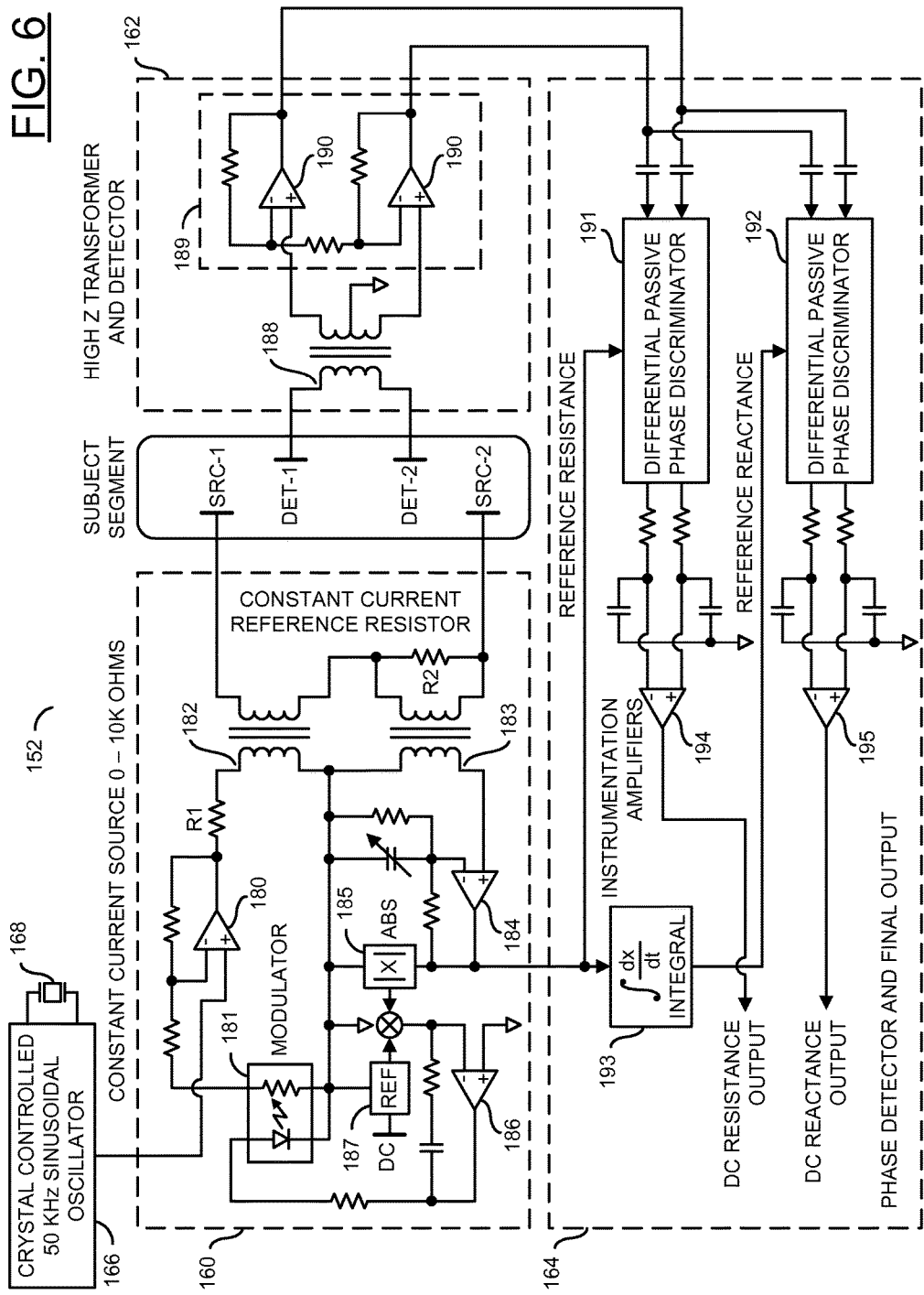
FIG. 6 is a diagram illustrating an example implementation of a BIA portion of the analysis circuit of FIG. 5.

Referring to FIG. 6, a diagram is shown illustrating an example implementation of the circuit 152 of FIG. 5. In various embodiments, the circuit 160 may receive a 50 KHz sinusoidal signal generated by a crystal controlled oscillator 166. The frequency of the sinusoidal signal from the crystal controlled oscillator 166 is determined by a crystal 168. However, other oscillator circuits may be implemented to meet the design criteria of a particular implementation. The circuit 160 is configured to maintain a current injected into the subject constant at a predetermined value (e.g., 425 microamps at 50 kHz). The maximum current should not exceed 500 microamps RMS at 50 kHz. To maintain a constant current, the circuit 160 supplies an input current to the subject (e.g., via the signals SRC-1 and SRC-2 of the interface 150), compares the current through the subject to a reference, and adjusts the input current based on the comparison. In one example, the circuit 160 implements a transformer coupled, open loop DC servo system that includes the oscillator 166, an amplifier 180, a modulator 181, a constant current input coupling transformer 182, a reference coupling transformer 183, a buffer amplifier 184, a rectifier 185, a summing amplifier 186, and a DC reference source 187.

The amplifier 180 is preferably configured as a non-inverting operational amplifier ("op-amp"). The sinusoidal output of the oscillator 166 is input into a non-inverting input of the amplifier 180 and an output of the amplifier 180 is coupled (fed back) to an inverting input through a resistor. A gain of the amplifier 180, and thus the current through the subject, is controlled by the modulator 181. The oscillator 166 can incorporate a conventional attenuator for the sinusoidal signal prior to the sinusoidal signal being presented to the amplifier 180.

The output of the amplifier 180 drives the constant current input coupling transformer 182, preferably through a series limiting resistor R1. The constant current input coupling transformer 182 supplies a current to the subject through electrodes connected to the interface 150. In one example, the constant current input coupling transformer 182 is implemented as a one-to-two transformer, where the primary is grounded, but the secondary is not.

A measuring circuit includes a constant current reference resistor R2, preferably a precision 1.0 kilo-ohm resistor, placed in the subject constant current path and coupled back to the remainder of the circuit 160 by the reference coupling transformer 183. In one example, the reference coupling transformer 183 is implemented as a one-to-one transformer, where the primary is ungrounded, but the secondary is grounded. Both the input coupling transformer 182 and the reference coupling transformer 183 should have an appropriate isolation barrier, such as a 500 volt DC isolation barrier. This configuration, together with the configuration of a detection transformer in the circuit 162, isolates the subject from all active circuitry.

The secondary of the reference coupling transformer 183 is coupled to a non-inverting input of the buffer amplifier 184. The buffer amplifier 184 is implemented, in one example, with a gain of preferably 6.5. An inverting input of the buffer amplifier 184 is grounded through a resistor in parallel with an adjustable capacitor. An output of the buffer amplifier 184 provides reference vectors for the circuit 164.

The output of the buffer amplifier 184, which is an indicator of the actual current flowing through the subject, is also used to derive a DC error signal used to control the modulator 181, which in turn controls the current through the subject to a predetermined value by controlling the gain of the amplifier 180. In various embodiments, the modulator 181 is an optocoupler including a light emitting diode (LED) optically coupled to a photocell. In one example, the photocell is a sealed cadmium sulfide (CdS) resistive conductor that changes resistance in response to light intensity from the LED. The DC error signal is supplied to an anode of the LED, while a cathode of the LED is grounded. The photocell resistance is high when the LED current is "off" and low when the LED current is "on". The resistive conductor is grounded on one end and connected to the inverting input of the amplifier 180 through another resistor. Although the modulator 181 could take the form of an FET, or some other device, an optocoupler is preferred because its use results in very little phase shift.

An output of the buffer amplifier 184 is rectified through a rectifier 185, producing a rectified voltage representing the actual current. The rectified voltage is compared in the summing amplifier 186 to a DC reference representing the desired current level. The DC reference is generated by a DC reference source 187. The summing amplifier 186 produces the DC error signal that drives the modulator 181. The DC error signal is a voltage that represents the difference between the actual current in the subject and the desired current. The DC reference source 187 should produce a very steady, fixed DC reference, preferably accomplished using a precision shunt regulator diode. In an alternative design, a standard Zener diode could be incorporated in place of the shunt regulator diode.

The summing amplifier 186 is a standard op-amp that compares the rectified signal from the rectifier 185 to the DC reference from the DC reference source 187. In one example, the summing amplifier 186 has a grounded non-inverting input. In one example, the precision rectified signal and the precision DC reference are supplied through resistors of the same value (e.g., 100 kilo-ohms) to the inverting input through a summing point, which point also includes the feedback supplied through a capacitor in series with a resistor to stabilize the constant current loop.

The detection of a voltage drop across the subject, and thus the first step in the measurement of the impedance, is performed by the circuit 162. In some embodiments, the circuit 162 includes a detection transformer 188 and an RF amplifier 189. The voltage drop across the subject is detected through electrodes connected to the DET-1 and DET-2 inputs of the interface 150. The unbalanced input from the subject is received at a primary of the detection transformer 188 and a balanced output is provided at a secondary of the detection transformer 188. In one example, the detection transformer 188 is a custom-wound transformer with an input impedance of greater than 2 mega-ohms at an operating frequency of 50 kHz. The detection transformer 188 provides no reference to ground in the subject, and the secondary is coupled to ground through a balanced center-tap.

The voltage from the secondary of the detection transformer 188 is amplified through the RF amplifier 189. In one example, the RF amplifier 189 comprises two op amps 190 configured as non-inverting common mode low-capacitance instrumentation amplifiers. Specifically, each tap from the secondary of the detection transformer 188 is connected to a non-inverting input of one of the op amps 190. The inverting inputs of the op amps 190 receive feedback through resistors, and the inverting inputs are coupled through another resistor, which controls the common mode gain. The subject variable differential outputs of the RF amplifier 189 are capacitively coupled to the circuit 164 through four coupling capacitors.

In some embodiments, the circuit 164 includes a phase detector 191 and a phase detector 192. Each of the phase detectors 191 and 192 is an identically designed balanced synchronous demodulator, except for the analog reference signal supplied to each. In one example, the phase detectors 191 and 192 are two passive analogue phase detectors that resolve the subject reactance and resistance obtained from the RF amplifier 189 through comparison to an analog reference reactance signal and an analog reference resistance signal. The output of each op amp 190 of the RF amplifier 189 provides one input to each of the phase detectors 191 and 192. Although the phase detectors shown are passive analogue detectors, an alternative embodiment can incorporate digital demodulators. However, the solid state demodulator is preferred for low power consumption and overall temperature stability.

As discussed previously, the output of the buffer amplifier 184 provides reference vectors for the circuit 164. Specifically, the buffer amplifier 184 provides a reference resistance vector and supplies an input into an integrator 193. The integrator 193 can be any standard device providing a 90 degree phase-shifted vector using the output of the buffer amplifier 184. An output of the integrator 193 provides a reference reactance vector. The reference resistance vector and the reference reactance vector supplied by the buffer amplifier 184 and the integrator 193, respectively, are each supplied to the phase detectors 191 and 192, respectively.

In general, the phase detectors 191 and 192 each include circuitry for demodulation and low pass filtering. The signals produced after demodulation and low pass filtering through the phase detectors 191 and 192 are two DC differential signals referenced to ground representing the resistance amplitude and two DC differential signals referenced to ground representing the reactance amplitude. These signals representing the resistance amplitude and the reactance amplitude are then converted to single-ended DC outputs by a pair of high quality instrumentation amplifiers 194 and 195. The resistance differential signals are input into the inverting and non-inverting inputs, respectively, of the amplifier 194, and the output of the amplifier 194 presents a DC Resistance Output signal. The reactance differential signals are input into the inverting and non-inverting inputs, respectively, of the amplifier 195, and an output of amplifier 195 presents a DC Reactance Output signal.

The resulting DC Resistance Output signal and DC Reactance Output signal from the instrumentation amplifiers 194 and 195 are supplied to the circuit 154, shown in FIG. 3. The DC Reactance Output signal and The DC Resistance Output signal could be, for example, voltage signals between zero and four volts, where four volts equals 2000 ohms.

Figure 7:
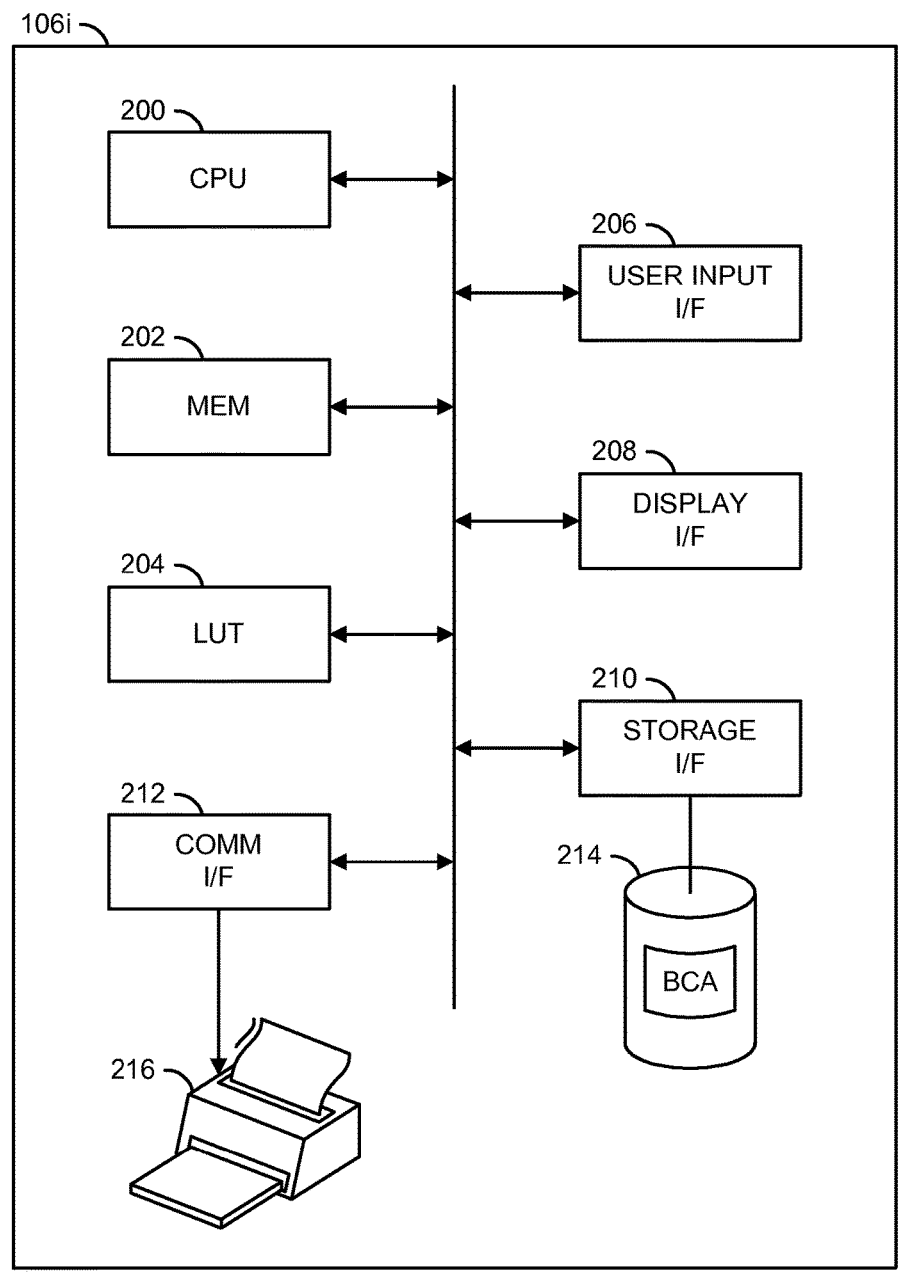
FIG. 7 is a diagram illustrating an example implementation of an electronic device of FIG. 1.

Referring to FIG. 7, a diagram is shown illustrating an example embodiment of an electronic device 106*i*. In various embodiments, the electronic device 106*i* may comprise a block (or circuit) 200, a block (or circuit) 202, a block (or circuit) 204, a block (or circuit) 206, a block (or circuit) 208, a block (or circuit) 210, a block (or circuit) 212, and a block (or circuit) 214. The block 200 may implement a processor or central processing unit (CPU). The block 202 may be implemented as one or more types of memory (e.g., RAM, ROM, FLASH, etc.). The block 204 may implement a lookup table (LUT) containing predetermined coefficients (e.g., SSCIs for a variety of specimens) for use in generating Certified Quality Numbers for various specimens in accordance with an embodiment of the invention. In some embodiments, the lookup table 204 may be implemented using a removable media (e.g., thumb drive, flash memory card, etc.) to allow easy update of the coefficients. In some embodiments, the electronic devices are configured to update (e.g., flash) an internal memory to update the predetermined coefficients. The block 206 may implement a user input interface (I/F) circuit. The block 208 may implement a display or display I/F circuit. The circuit 210 may implement a storage interface (I/F) circuit. The circuit 212 may implement a communications interface (I/F) circuit. In one example, the block 210 may couple the electronic device 106*i* to one or more types of storage media (e.g., hard disk drive, flash drive, cloud storage, etc.) 214. In one example, the block 212 may couple the electronic device 106*i* to a printer 216.

The electronic device 106*i* may be controlled by an operating system (e.g., Microsoft Windows, Apple OS, Ubuntu, Linux, etc.) loaded from the storage media 214 and executed by the circuit 200. In various embodiments, the electronic devices 106*a*-106*n* store the number of predetermined coefficients used in computing the Certified Quality Number in the lookup table 204. Each of the predetermined coefficients represents a species specific cell integrity value determined, for example, through testing of various species grouped according to various characteristics. The block 212 may be configured to receive the specimen information and the resistance and reactance values from the analysis circuit 104 and to produce the Certified Quality Number analysis reports in accordance with an embodiment of the invention using the printer 216.

Figure 8:
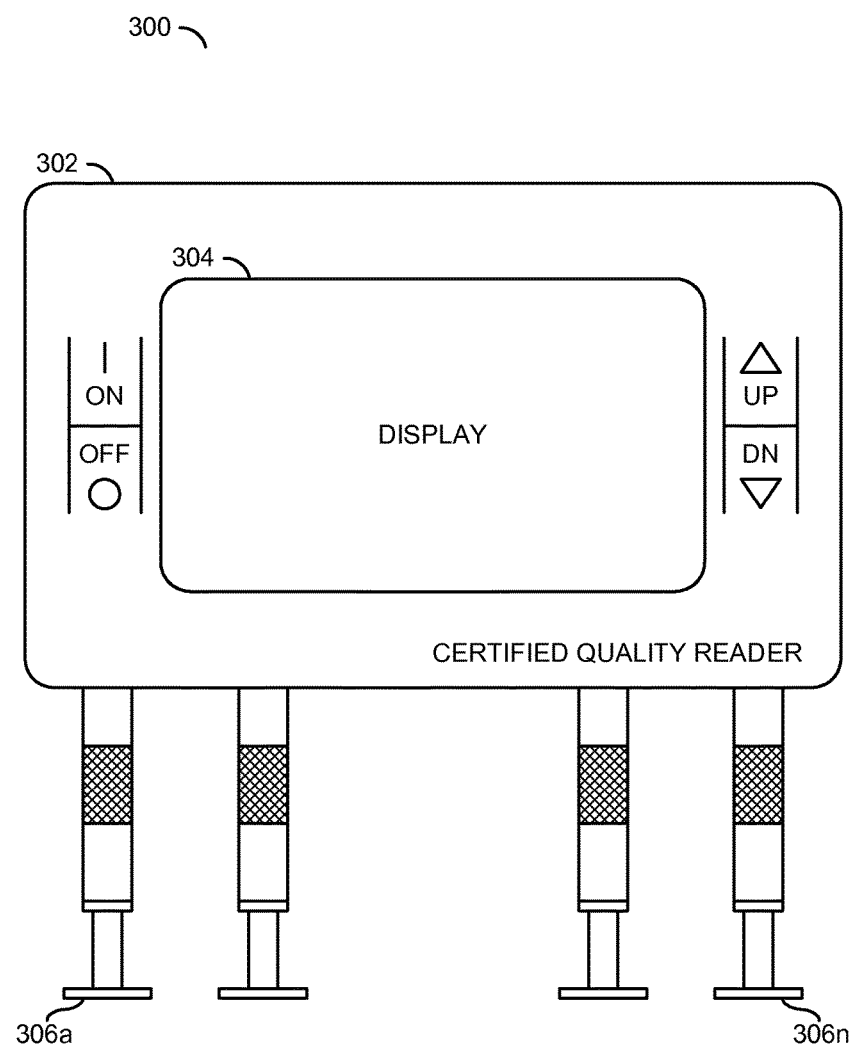
FIG. 8 is a diagram illustrating a handheld reader in accordance with an embodiment of the invention.

Referring to FIG. 8, a diagram is shown illustrating a handheld reader 300 in accordance with an embodiment of the invention. In various embodiments, the handheld reader 300 may comprise a housing 302, a display 304, and a set of compression electrodes 306*a*-306*n*. The housing 302 and display 304 are generally configured for the particular environment in which the handheld reader 300 is expected to function. In some embodiments, the housing 302 may be implemented as a simple plastic (e.g., polystyrene, etc.) case. In embodiments for use in hostile or hazardous environments (e.g., at sea, etc.), the housing 302 and display 304 may be implemented as a ruggedized (or hardened) case. For example, the housing 302 may be implemented as a metal (e.g., magnesium, etc.) casting including a gasket to hermetically seal the contents (e.g., printed circuit board, integrated circuits, etc.) from the external environment. In one example, the housing 302 may include a rubber or silicone covering to provide waterproofing and drop resistance. The housing 302 may include hermetically sealed connections for coupling to the electrodes 306*a*-306*n*. For example, the electrodes 306*a*-306*n* may comprise 10-32 tapped holes that may be threaded onto studs extending from the housing 302.

The handheld reader 300 may include a number of sealed buttons, which may allow, inter alia, (i) a user to switch the handheld reader 300 "on" or "off", (ii) the user to move up or down through menus and/or measurement logs, etc., (iii) the user to enter information regarding specimen being tested. The handheld reader 300 may include an audible indicator that may be programmed to sound when the CQN of a specimen exceeds a predefined threshold. The audible indicator may allow faster assessments by allowing a user to avoid reading the CQN from the display for each measurement.

Figure 9:
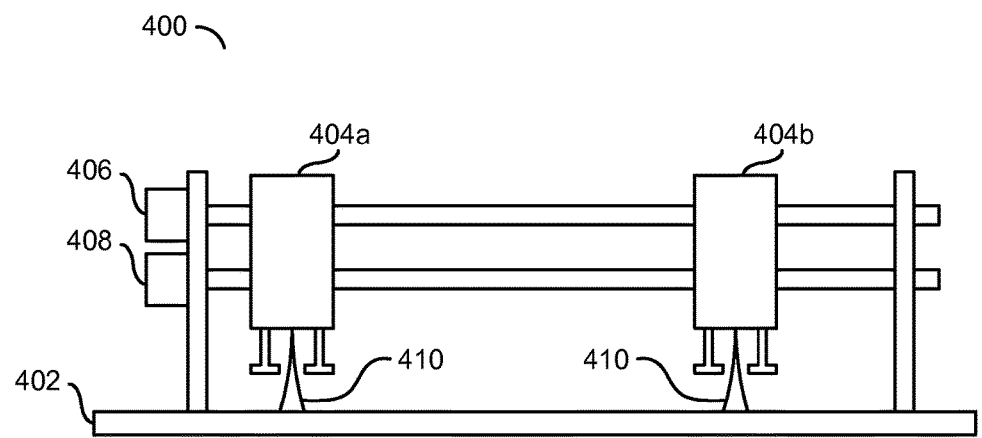
FIG. 9 is a diagram illustrating an example apparatus combining length measurement and certified quality number generation in accordance with an embodiment of the invention.

Referring to FIG. 9, a diagram is shown illustrating an example apparatus for measuring length and Certified Quality Number in accordance with an embodiment of the invention. In some embodiments, an apparatus 400 may be implemented allowing accurate measurement of a length of a specimen (e.g., a fish) and accurate placement of electrodes for making the bioelectrical impedance measurements for generating the Certified Quality Number. In various embodiments, the apparatus 400 may comprise a table (or base) 402, a pair of electrode modules 404*a* and 404*b*, a first position sensor 406, and a second position sensor 408. In some embodiments, the position sensors 406 and 408 may be implemented as variable reluctance sensors.

In one example, the electrode module 404*a* may be placed at a first position over the specimen to be measured and the electrode module 404*b* may be placed at a second position over the specimen to be measured. In one example, the electrode modules 404*a* and 404*b* may be accurately positioned according to features of the specimen using laser guides 410. The position sensors 406 and 408 may be used to accurately determine a distance between the electrode modules 404*a* and 404*b* and, therefore, the distance between respective sensing electrodes of the electrode modules 404*a* and 404*b*. The electrode modules 404*a* and 404*b* are lowered until the electrodes are compressed to the appropriate amount and the bioelectrical impedance measurements made.

Figure 10:
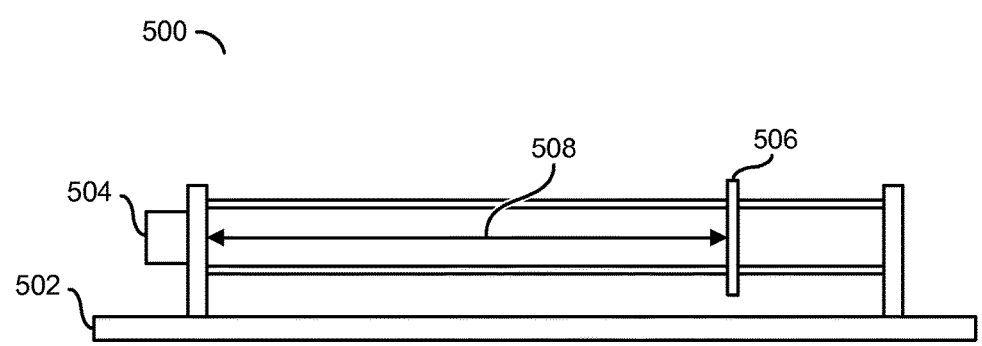
FIG. 10 is a diagram illustrating an apparatus for measuring length of a food specimen in accordance with an example embodiment of the invention.

Referring to FIG. 10, a diagram is shown illustrating an apparatus for measuring a length of a food specimen in accordance with another example embodiment of the invention. In some embodiments, an apparatus 500 may be implemented to facilitate accurate measurement of a length of a specimen (e.g., a fish, etc.). The apparatus 500 may be used in conjunction with the handheld reader 300 of FIG. 8 to obtain an accurate length measurement and accurate placement of electrodes for making bioelectrical impedance measurements for generating the Certified Quality Number for the specimen. In various embodiments, the apparatus 500 may comprise a table (or base) 502, a sensor 504, and a flag 506. In various embodiments, the sensor 504 may be configured to measure distance using either ultrasound or laser light.

In one example, a specimen (e.g., a fish, etc.) may be placed on the base 502 such that a first feature of the specimen that defines a length of the specimen is aligned with the sensor 504. The flag 506 may be moved to a position corresponding to a second feature of the specimen defining the length of the specimen. The sensor 504 then determines of the specimen by measuring the distance 508 to the flag 506. Once the length is measured, the handheld reader 300 may be used to determine the corresponding Certified Quality Number for the specimen.

Figure 11:
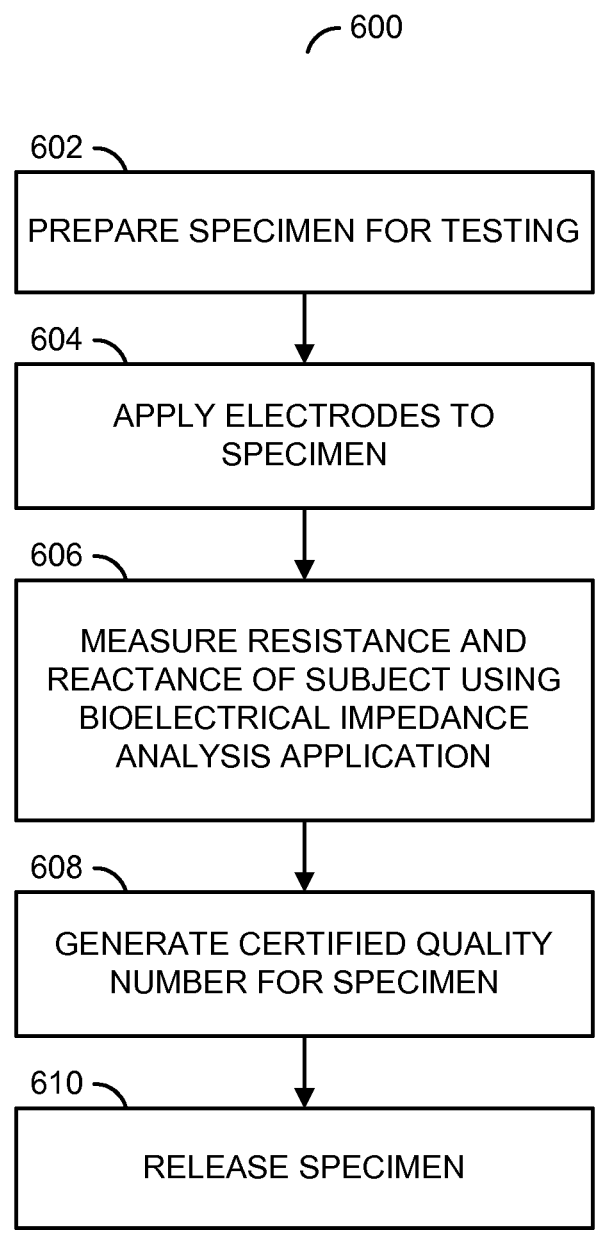
FIG. 11 is a flow diagram illustrating a process in accordance with an embodiment of the invention.

Referring to FIG. 11, a flow diagram of a process 600 is shown illustrating a process in accordance with an example embodiment of the present invention. In some embodiments, the process (or method) 600 may comprise a step (or state) 602, a step (or state) 604, a step (or state) 606, a step (or state) 608, and a step (or state) 610. In the step 602, a specimen (e.g., a fish, a piece of beef or chicken, a produce item, etc.)) is prepared for testing by positioning the subject on a non-conductive surface with a lateral surface facing up. In the step 604, a compression electrode assembly is applied in a predetermined manner to the specimen. For example, in an embodiment measuring certified quality number of a fish specimen, the compression electrode assembly may be applied (i) midway between a lateral line and a base of a dorsal fin and an adipose fin and (ii) between a posterior edge of the operculum and a leading edge of the adipose fin. The electrode assembly is pressed against the specimen until the compression electrodes are compressed to about 50% of a fully compressed position. In the step 606, a measurement cycle is started to collect resistance and reactance measurements, which are subsequently used to generate a Certified Quality Number for the specimen. In various embodiments, the resistance and reactance measurements are transferred to an electronic device (e.g., a PC, etc.) or time and date stamped and stored in the analysis circuit for later transfer to the electronic device (e.g., en masse) via a communication link (e.g., a USB connection, a WiFi connection, a BLUETOOTH (BT) connection, a flash card, a thumb drive, etc.). In the step 608, the resistance and reactance measurements are used, by an application program, to generate the certified quality number for the specimen (e.g., indicative of the cellular integrity of the specimen). In the step 610, the specimen is removed from the testing station.

Figure 12:
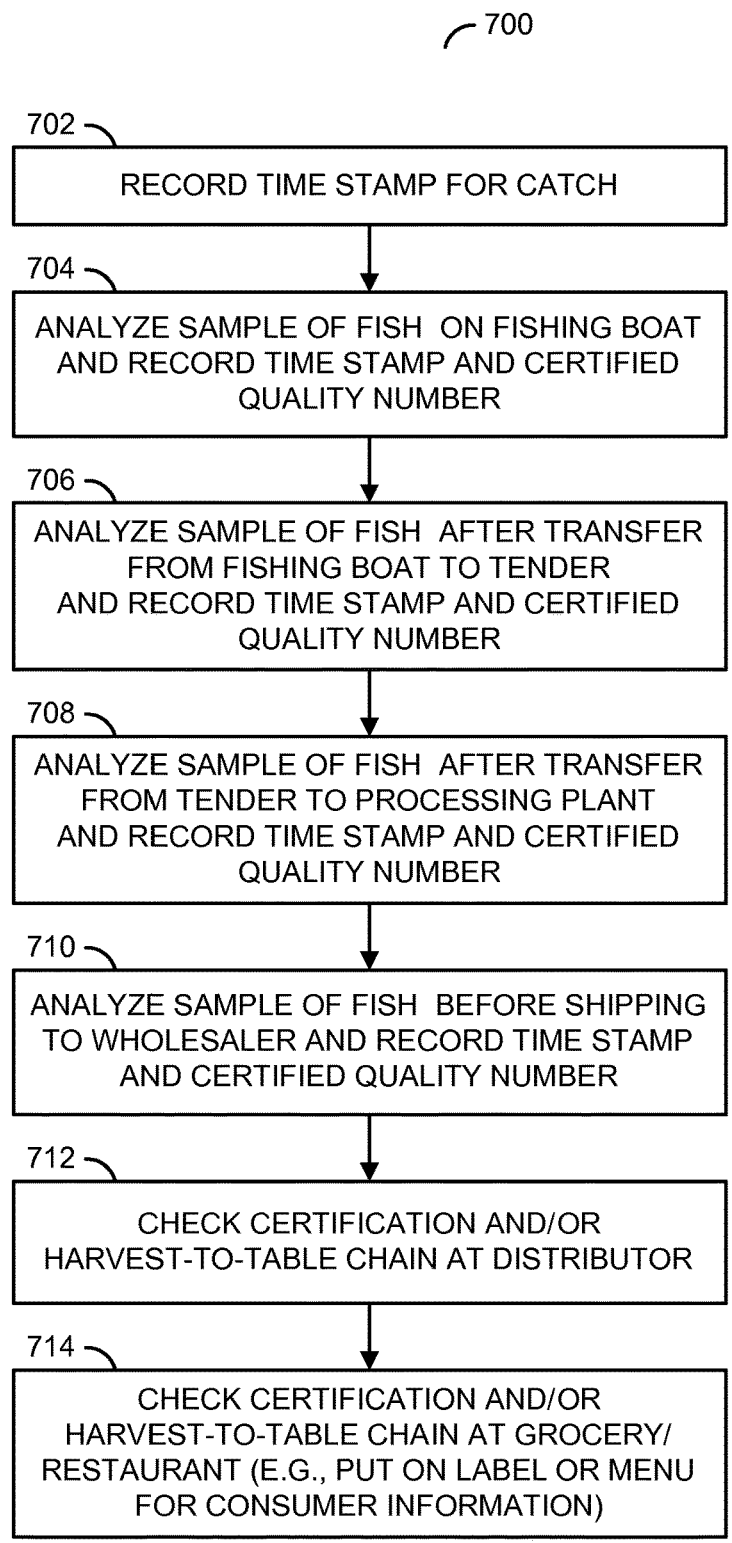
FIG. 12 is a flow diagram illustrating an example harvest-to-table certification chain in accordance with an embodiment of the invention.

Referring to FIG. 12, a flow diagram of a process 700 is shown illustrating an example harvest-to-table certification chain in accordance with an embodiment of the invention. Although an example is described using seafood, a similar process may be applied to other food specimens, including but not limited to beef, chicken, lamb, produce, etc. Just as a chain of custody is important to ensure integrity of evidence, a harvest-to-table certification chain may be implemented to ensure quality and integrity of seafood (or other food for human consumption). In some embodiments, the process (or method) 700 may comprise a step (or state) 702, a step (or state) 704, a step (or state) 706, a step (or state) 708, a step (or state) 710, a step (or state) 712, and a step (or state) 714. In the step 702, a time stamp (e.g., time, location, etc.) is recorded when a specimen (e.g., a fish) is caught. In the step 704, a sample of the fish caught on a fishing boat are analyzed and certified quality numbers and time stamps are recorded on the fishing boat. In the step 706, a sample of fish transferred from a fishing boat to a tender are analyzed and certified quality numbers and time stamps are recorded on the tender. In the step 708, a sample of fish transferred from a tender to a processing plant are analyzed and certified quality numbers and time stamps are recorded. In the step 710, a sample of fish about to be shipped to a wholesaler are analyzed and certified quality numbers and time stamps are recorded. In the step 712, previously recorded certified quality numbers and time stamps are checked by a distributor. In the step 714, previously recorded certified quality numbers and time stamps are checked by grocery stores and/or restaurants providing the seafood to customers. In one example, the grocery stores may put the certification information on seafood labels and the restaurant may put the certification information on a menu, as a way of informing and/or ensuring customers of the integrity and/or quality of the seafood.

In one example, each tester at each stage in the process 700 may use their own reader. Each of the readers generally has the same electrode spacing and lookup table. By providing each tester with their own handheld unit, the integrity of the certification process may be enhanced by reducing the possibility of a single device being tampered with to provide better numbers or a malfunctioning unit not being detected.

Figure 13:
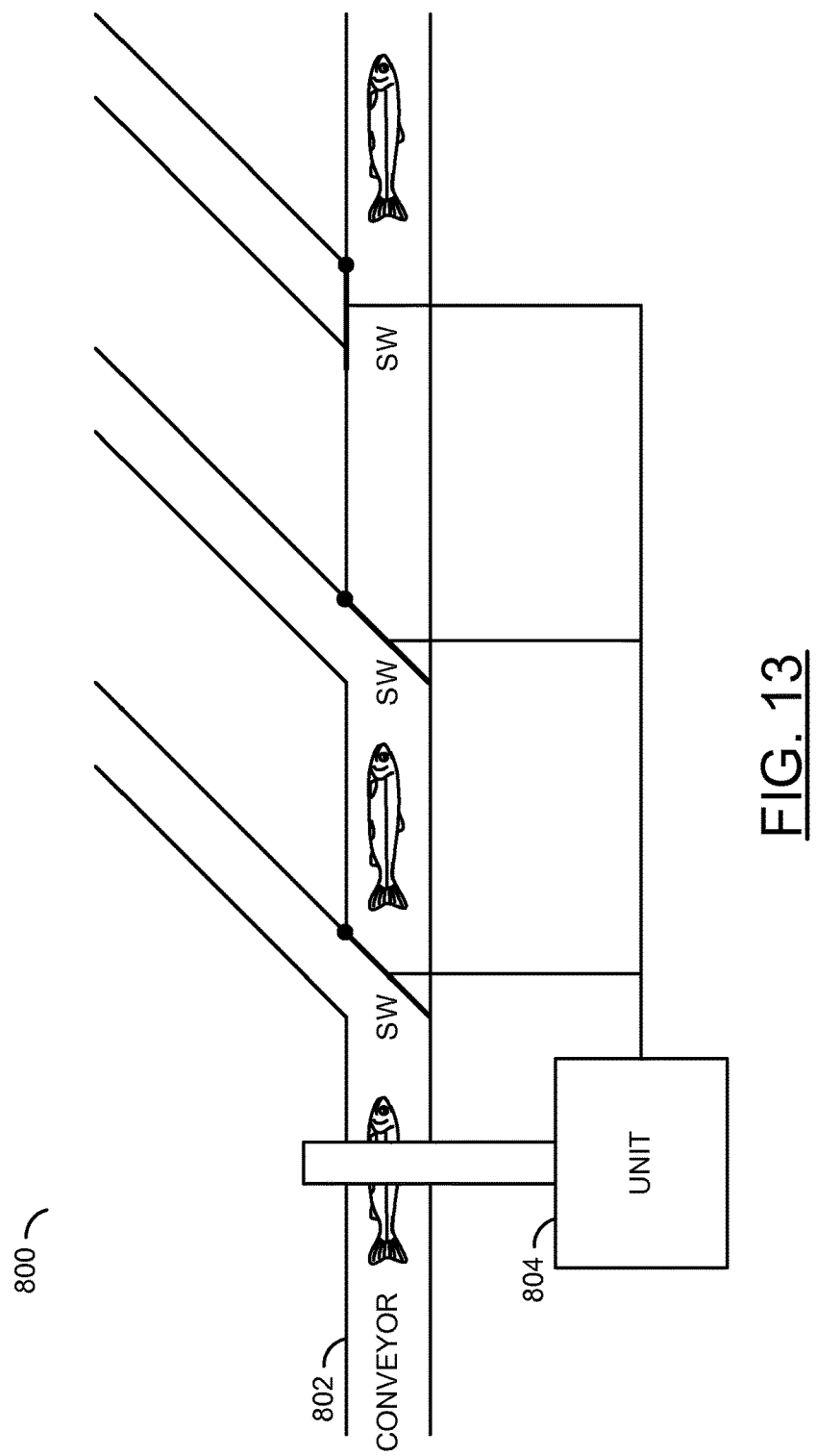
FIG. 13 is a diagram illustrating an example conveyor system with an integrated bioelectrical analysis system in accordance with another example embodiment of the invention.

Referring to FIG. 13, a diagram is shown illustrating a conveyor system 800 with an integrated bioelectrical analysis system in accordance with another example embodiment of the invention. In one example, fish may be placed on a conveyor 802 for sorting. An electrical measurement of a fish is instantaneous and can be built into processing equipment so every fish that enters a plant can be measured. The complete individual fish certification would include the length, weight, and Certified Quality Number before the fish is frozen or sold. In some embodiments, the Certified Quality Number generated by the analysis system may be used to control (e.g., via switches SW) a particular conveyor path each fish takes following analysis.

The functions illustrated by the diagrams of FIGS. 1-13 may be implemented using one or more of a conventional general purpose processor, digital computer, microprocessor, microcontroller, RISC (reduced instruction set computer) processor, CISC (complex instruction set computer) processor, SIMD (single instruction multiple data) processor, signal processor, central processing unit (CPU), arithmetic logic unit (ALU), video digital signal processor (VDSP) and/or similar computational machines, programmed according to the teachings of the specification, as will be apparent to those skilled in the relevant art(s). Appropriate software, firmware, coding, routines, instructions, opcodes, microcode, and/or program modules may readily be prepared by skilled programmers based on the teachings of the disclosure, as will also be apparent to those skilled in the relevant art(s). The software is generally executed from a medium or several media by one or more of the processors of the machine implementation.

The invention may also be implemented by the preparation of ASICs (application specific integrated circuits), Platform ASICs, FPGAs (field programmable gate arrays), PLDs (programmable logic devices), CPLDs (complex programmable logic devices), sea-of-gates, RFICs (radio frequency integrated circuits), ASSPs (application specific standard products), one or more monolithic integrated circuits, one or more chips or die arranged as flip-chip modules and/or multi-chip modules or by interconnecting an appropriate network of conventional component circuits, as is described herein, modifications of which will be readily apparent to those skilled in the art(s).

The invention thus may also include a computer product which may be a storage medium or media and/or a transmission medium or media including instructions which may be used to program a machine to perform one or more processes or methods in accordance with the invention. Execution of instructions contained in the computer product by the machine, along with operations of surrounding circuitry, may transform input data into one or more files on the storage medium and/or one or more output signals representative of a physical object or substance, such as an audio and/or visual depiction. The storage medium may include, but is not limited to, any type of disk including floppy disk, hard drive, magnetic disk, optical disk, CD-ROM, DVD and magneto-optical disks and circuits such as ROMs (read-only memories), RAMs (random access memories), EPROMs (erasable programmable ROMs), EEPROMs (electrically erasable programmable ROMs), UVPROM (ultra-violet erasable programmable ROMs), Flash memory, magnetic cards, optical cards, and/or any type of media suitable for storing electronic instructions.

The terms "may" and "generally" when used herein in conjunction with "is(are)" and verbs are meant to communicate the intention that the description is exemplary and believed to be broad enough to encompass both the specific examples presented in the disclosure as well as alternative examples that could be derived based on the disclosure. The terms "may" and "generally" as used herein should not be construed to necessarily imply the desirability or possibility of omitting a corresponding element.

While the invention has been particularly shown and described with reference to the preferred embodiments thereof, it will be understood by those skilled in the art that various changes in form and details may be made without departing from the scope of the invention.

The invention claimed is:

1. An apparatus comprising:
  an array of compression electrodes arranged in a line and comprising a pair of outer compression electrodes and a pair of inner compression electrodes disposed between said outer compression electrodes, each of said compression electrodes comprising a contact pad and a threaded portion, and configured to individually compress to follow a contour of an object while maintaining contact of said contact pad with a surface of said object while said apparatus is pressed against said object, wherein said compression electrodes are non-piercing, non-damaging, and non-contaminating;
  an analysis circuit configured to automatically make a bioelectrical impedance measurement using said array of compression electrodes and compute a value representative of a cell integrity of said object based upon said bioelectrical impedance measurement, object-related information, and a plurality of values in a lookup table, wherein said analysis circuit configures said pair of outer compression electrodes as signal injection electrodes and said pair of inner compression electrodes as detecting electrodes; and
  a housing enclosing said analysis circuit and including a plurality of hermetically sealed threaded connections, wherein said hermetically sealed threaded connections are electrically coupled to said analysis circuit and enable the threaded portion of each of said compression electrodes to be removably connected to the housing and electrically connected to the analysis circuit.

2. The apparatus according to claim 1, wherein said value comprises a Certified Quality Number.

3. The apparatus according to claim 1, wherein said value representative of said cell integrity of said object is based upon a predetermined species specific coefficient and a ratio of capacitive reactance to resistance of the object.

4. The apparatus according to claim 1, wherein said object comprises at least one of a seafood specimen, a fish, a fish fillet, and a body part of a fish.

5. The apparatus according to claim 1, wherein said object comprises at least one of a foodstuff specimen, a protein specimen, and a produce specimen.

6. The apparatus according to claim 1, wherein said compression electrodes enable said bioelectrical impedance measurement to be non-invasive to said object.

7. The apparatus according to claim 1, wherein said compression electrodes enable said bioelectrical impedance measurement to be made through at least one of skin, rind, flesh, and fish scales.

8. The apparatus according to claim 1, wherein said compression electrodes enable said bioelectrical measurement to be independent of an operator making the measurement.

9. The apparatus according to claim 1, wherein a distance between adjacent inner and outer compression electrodes is fixed at a predetermined value and a distance between said pair of inner compression electrodes is set according to said object.

10. The apparatus according to claim 1, further comprising a controller configured to control a conveyor system in response to said value.

11. The apparatus according to claim 1, wherein said values in said lookup table correlate bioelectrical impedance measurements and one or more of fish species, plant species, and animal species.

12. The apparatus according to claim 1, wherein each of said compression electrodes further comprises:
  a three-eighths inch by one-and-seven-eighths inch stainless steel cylinder with an internal diameter (ID) of about three-tenths of an inch; and
  a one-quarter inch by one-and-one-eighth inch stainless steel rod attached to said contact pad.

13. The apparatus according to claim 12, wherein said contact pad is about five-eighths of an inch in diameter and attached to said stainless steel rod by a 6-32 stainless steel flat head screw.

14. The apparatus according to claim 12, wherein each of said compression electrodes further comprises:
  a bronze bushing, through which said stainless steel rod passes, press fit into a first end of said stainless steel cylinder;
  a three-eighths inch by three-eighths inch stainless steel end cap comprising said thread portion press fit into a second end of said stainless steel cylinder; and
  a stainless steel spring disposed within said stainless steel cylinder between said stainless steel end cap and said bronze bushing, wherein said stainless steel rod is configured to compress said stainless steel spring when said contact pad is pressed against said surface of said object.

15. The apparatus according to claim 14, wherein said stainless steel spring provides a compressive force of about 200 grams.

16. The apparatus according to claim 1, wherein said object-related information comprises one or more of length, weight, species, age, and gender.

17. A method of generating a food quality rating comprising the steps of:
applying an array of compression electrodes along a contour of a food specimen, said array of compression electrodes arranged in a line and comprising a pair of outer compression electrodes and a pair of inner compression electrodes disposed between said outer compression electrodes, each of said compression electrodes comprising a contact pad and a threaded portion, and configured to individually compress to follow said contour of said food specimen while maintaining contact of said contact pad with a surface of said food specimen while said array of compression electrodes is pressed against said food specimen, wherein said compression electrodes are connected to a housing enclosing an analysis circuit by a plurality of hermetically sealed threaded connections, said hermetically sealed threaded connections enabling the threaded portion of each of said compression electrodes to be removably connected to the housing and electrically connected to the analysis circuit, and said compression electrodes are non-piercing, non-damaging, and non-contaminating;
making a bioelectrical impedance measurement on said food specimen using said array of compression electrodes and said analysis circuit, wherein said pair of outer compression electrodes are configured as signal injection electrodes and said pair of inner compression electrodes are configured as detecting electrodes; and
automatically computing, with said analysis circuit, a value representing a cell integrity of said food specimen using said bioelectrical impedance measurement, food specimen related information, and a plurality of values in a lookup table correlating bioelectrical impedance measurements and one or more of fish species, plant species, and animal species.

18. The method according to claim 17, wherein a contour of a seafood specimen (i) runs from a posterior edge of an operculum of said seafood specimen to a leading edge of an adipose fin of said seafood specimen and (ii) lies between a lateral line of said seafood specimen and a base of a dorsal fin of said seafood specimen.

19. The method according to claim 18, wherein:
an anterior inner compression electrode is positioned between said posterior edge of said operculum of said seafood specimen and a leading edge of said dorsal fin; and
a posterior outer compression electrode is positioned at said leading edge of said adipose fin of said seafood specimen and between said lateral line of said seafood specimen and a base of said adipose fin of said seafood specimen.

20. The method according to claim 18, wherein said bioelectrical impedance measurement is made on said seafood specimen with said array of compression electrodes compressed about 50 percent.

* * * * *